(12) United States Patent
Buynak et al.

(10) Patent No.: US 11,234,966 B2
(45) Date of Patent: *Feb. 1, 2022

(54) C5-SUBSTITUTED CARBAPENEM ANTIBIOTICS, COMPOSITIONS CONTAINING SUCH COMPOUNDS, AND METHODS OF USE IN TREATMENT OF MYCOBACTERIUM TUBERCULOSIS AND NON-TUBERCULAR MYCOBACTERIA

(71) Applicants: Southern Methodist University, Dallas, TX (US); University of Central Florida Research Foundation, Inc., Orlando, FL (US)

(72) Inventors: John D. Buynak, Dallas, TX (US); Noora M. S. A. Al-Kharji, Richardson, TX (US); Weirui Chai, Chicago, IL (US); Thu Q. Nguyen, North Richland Hills, TX (US); Maha Alqurafi, Dallas, TX (US); Kyle Rohde, Orlando, FL (US); Rashmi Gupta, Lake Mary, FL (US)

(73) Assignees: Southern Methodist University, Dallas, TX (US); University of Central Florida Research Foundation, Inc., Orlando, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/879,892

(22) Filed: May 21, 2020

(65) Prior Publication Data

US 2020/0281894 A1 Sep. 10, 2020

Related U.S. Application Data

(63) Continuation of application No. 16/006,374, filed on Jun. 12, 2018, now Pat. No. 10,702,501.

(60) Provisional application No. 62/518,569, filed on Jun. 12, 2017.

(51) Int. Cl.

| C07D 477/06 | (2006.01) |
| *A61K 31/407* | (2006.01) |
| C07D 477/00 | (2006.01) |
| *A61K 45/06* | (2006.01) |
| C07D 477/04 | (2006.01) |
| C07D 477/20 | (2006.01) |

(52) U.S. Cl.
CPC ............ *A61K 31/407* (2013.01); *A61K 45/06* (2013.01); *C07D 477/00* (2013.01); *C07D 477/04* (2013.01); *C07D 477/06* (2013.01); *C07D 477/20* (2013.01)

(58) Field of Classification Search
CPC .................................................. C07D 477/06
See application file for complete search history.

(56) References Cited

U.S. PATENT DOCUMENTS

| 10,519,161 B2* | 12/2019 | Buynak | ................ C07D 477/14 |
| 10,702,501 B2* | 7/2020 | Buynak | ................ C07D 477/06 |
| 2014/0121192 A1 | 5/2014 | Buynak | |

OTHER PUBLICATIONS

Aitha, M., et al., "Investigating the position of the hairpin loop in New Delhi metallo-β-lactamase, NDM-1, during catalysis and inhibitor binding." J. Inorg. Biochem. (2016), 156:35-39.

Amudhan S.M.., et al., "OXA beta-lactamase-mediated carbapenem resistance in Acinetobacter baumannii." Indian J. Med. Microbiol. (2011) 29:269-74.

Andreu N., et al., "Optimisation of bioluminescent reporters for use with mycobacteria." PLoS One (2010), 5:e10777.

Arain, T. M., et al., "Bioluminescence screening in vitro (Bio-Siv) assays for high-volume antimycobacterial drug discovery." Antimicrob. Agents Chemother. (1996), 40:1536-1541.

(Continued)

*Primary Examiner* — Paul V Ward
(74) *Attorney, Agent, or Firm* — Edwin S. Flores; Chalker Flores, LLP

(57) ABSTRACT

The present invention includes a composition, method of making and method of using a novel C5-substituted carbapenem antibiotic of formula 1:

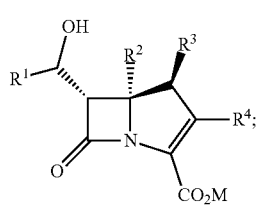

$R^1$ is H or $CH_3$ $R^2$ is not H, and is $CH_3$, or C1-C6 straight chain, or branched alkyl, or C3-C6 cycloalkyl group, or unsaturated alkenyl, including $C=CH_2$;

$R^3$ is H, $CH_3$, or a C1-C6 alkyl or cycloalkyl group, a heteroatom-substituted alkyl; and $R^4$ is a C1 to C6 alkyl, or substituted alkyl group, especially including substituents which possess positive charge, or a hydroxyl group; or $R^4$ is an $SR^a$, where $R^a$ is an unsubstituted C1 to C6 alkyl group, a substituted C1 to C6 alkyl group, or a functional group that is positively charged, or which bears a positive charge when in aqueous solution at pH 7; or $R^4$ is a $CH_2OR^b$, where $R^b$=C1 to C6 alkyl or substituted alkyl groups, substituted or unsubstituted aryl, or a heteroaryl groups.

22 Claims, 1 Drawing Sheet

(56) References Cited

OTHER PUBLICATIONS

Bajaj, H.; Scorciapino, M. A.; Moynie, L.; Page, M. G. P.; Naismith, J. H.; Ceccarelli, M.; Winterhalter, M. Molecular basis of filtering carbapenems by porins from β-lactam-resistant clinical strains of *Escherichia coli*. J. Biol. Chem. (2016), 291:2837-2847.

Biswas S., et al., "Structural insight into OprD substrate specificity." Nat. Struct. Mol. Biol. (2007), 14:1108-1109.

Carroll, P., et al., "Sensitive detection of gene expression in mycobacteria under replicating and non-replicating conditions using optimized far-red reporters " PLoS One (2010), 5:e9823.

Deb, C., et al., "A novel in vitro multiple-stress dormancy model for *Mycobacterium tuberculosis* generates a lipid-loaded, drug-tolerant, dormant pathogen." PLoS One (2009), 4:e6077.

Dubee, V., et al., "Inactivation of *Mycobacterium tuberculosis* L,D-transpeptidase LdtMH by carbapenems and cephalosporins." Antimicrob. Agents Chemother. (2012), 56:4189-4195.

Esterly J. S., et al., "Evaluation of clinical outcomes in patients with bloodstream infections due to Gram-negative bacteria according to carbapenem MIC stratification." Antimicrob. Agents Chemother. (2012), 56:4885-4890.

Evans, B., et al., "OXA b-lactamases." Clin. Microbiol. Rev. (2014), 27:241-263.

Flores, A. R., et al., "Genetic analysis of the beta-lactamases of *Mycobacterium tuberculosis* and *Mycobacterium smegmatis* and susceptibility to beta-lactam antibiotics Microbiology." (2005), 151(Pt 2) :521-32.

Gao, K., et al., "A Network of Conformational Transitions in the Apo form of NDM-1 Enzyme Revealed by MD simulation and a Markov State Model." J. Phys. Chem B. (2017), 121:2952-2960.

Hancock, R. E. W., et al., "Function of Psedomonas Porins in Uptake and Efflux." Ann. Rev. Microbiol. (2002):56, 17-38.

Hazra, S., et al., "Kinetic and Structural Characterization of the Interaction of 6-Methylidene Penem 2 with the β-Lactamase from *Mycobacterium tuberculosis*." Biochemistry (2015), 54:5657-5664.

Homolka, S., et al., "Functional genetic diversity among *Mycobacterium tuberculosis* complex clinical isolates: delineation of conserved core and lineage-specific transcriptomes during intracellular survival." PLoS Pathog. (2010), 6:e1000988.

Hugonnet, J.E., et al., "Meropenem-clavulanate is effective against extensively drug-resistant *Mycobacterium tuberculosis*." Science (2009), 323:1215-1218.

Hugonnet J.E., et al., "Factors essential for L,D-transpeptidase-mediated peptidoglycan cross-linking and β-lactam resistance in *Escherichia coli*." Elife (2016), 5:e 19469.

Iannazzo, L., et al., "Routes of Synthesis of Carbapenems for Optimizing Both the Inactivation of L,D-Transpeptidase LdtMt1 of *Mycobacterium tuberculosis* and the Stability toward Hydrolysis by β-Lactamase BlaC." J. Med. Chem. (2016), 59:3428-3428.

Isabella, V. M., et al., "Toward the rational design of carbapenem uptake in Pseudomonas aeruginosa." Chem. Biol. (2015), 22: 535-547.

Jarand J., et al., "Clinical and microbiologic outcomes in patients receiving treatment for *Mycobacterium abscessus* pulmonary disease." Clin. Infect. Dis. (2011), 52:565-571.

Karah, N., et al., "Insights into the global molecular epidemiology of carbapenem non-susceptible clones of Acinetobacter baumannii." Drug Resist. Updat. (2012), 15:237-247.

Kim, H. S., et al., "Structural basis for the inhibition of *Mycobacterium tuberculosis* L,D-transpeptidase by meropenem, a drug effective against extensively drug-resistant strains." Acta cryst.. Sect. D, Biol. cryst. (2013), 69(Pt 3) :420-31.

Kocaoglu, O.; Carlson, E. E. Profiling of b-lactam selectivity for penicillin-binding proteins in *Escherichia coli* strain DC2. Antimicrob Agents Chemother (2015), 59:2785-2790.

Lavollay, M., et al., "The peptidoglycan of stationary-phase *Mycobacterium tuberculosis* predominantly contains cross-links generated by L,D-transpeptidation." J. Bacteriol. (2008), 190:4360-4366.

Lee, K., et al., "Multidrug-resistant *Acinetobacter* spp.: increasingly problematic nosocomial pathogens." Yonsei Med. J. (2011), 52:879-891.

Leonard, D. A., et al., "Class D β-Lactamases: A Reappraisal after Five Decades." Acc. Chem. Res. (2013), 46:2407-2415.

Locher, C. P., et al., "A novel inhibitor of gyrase B is a potent drug candidate for treatment of tuberculosis and nontuberculosis mycobacterial infections." Antimicrob Agents Chemother (2015), 59:1455-1465.

Logan, L. K. "Carbapenem-Resistant Enterobacteriaceae: An Emerging Problem in Children." Clin. Infect.Dis. (2012), 55:852-859.

Lohans, C. T., et al., "A New Mechanism for β-Lactamases: Class D Enzymes Degrade 1β-Methyl Carbapenems through Lactone Formation." Angew. Chem. Int. Ed. (2018), 57:1282-1285.

Mainardi, J.-L., et al., "Novel mechanism of β-lactam resistance due to bypass of DD-transpeptidation in Enterococcus faecium." J. Biol Chemm (2000), 275:16490-16496.

Makena, A., et al., "Comparison of Verona Integron-Borne Metallo-β-Lactamase (VIM) variants reveals differences in stability and inhibition profiles" Antimicrob. Agents Chemother. (2016), 60:1377-1384.

Maxsom, T., et al., "Targeted treatment for bacterial infections: prospects for pathogen-specific antibiotics coupled with rapid diagnostics." Tetrahedron (2016), 72:3609-3624.

Mendes, R. E., et al., "Emergence and widespread dissemination of OXA-23, -24/40 and -58 carbapenemases among *Acinetobacter* spp. in Asia-Pacific nations: Report from the SENTRY Surveillance Program." J. Antimicrob. Chemother. (2009), 63:55-59.

Modi, S. R., et al., "Antibiotics and the gut microbiota." J. Clin. Invest. (2014), 124:4212-4218.

Mor, N., et al., "Comparison of activities of rifapentine and rifampin against *Mycobacterium tuberculosis* residing in human macrophages." Antimicrob Agents Chemother (1995), 39:2073-2077.

Muller, B., et al., "The heterogeneous evolution of multidrug-resistant *Mycobacterium tuberculosis*." Trends Genet. (2013), 29:160-169.

Munagala, G., et al., "Synthesis of new generation triazolyl- and isoxazolyl- containing 6-nitro-2,3-dihydroimidazooxazoles as anti-TB agents: in vitro, structure-activity relationship, pharmacokinetics and in vivo evaluation." Org. Biomol. Chem. (2015), 13:3610-3624.

Nessar R., et al., "*Mycobacterium abscessus:* a new antibiotic nightmare." J. Antimicrob. Chemother. (2012), 67:810-8.

Nordmann, P., et al., "Global spread of carapeneamse producing Enterobacteriaceae." Emerg Infect Dis. (2011), 17:1791-1798.

Papp-Wallace, K. M., et al., "Variants of β-lactamase KPC-2 that are resistant to inhibition by avibactam." Antimicrob. Agents Chemother. (2015), 59:3710-3717.

Patel, T. S.; Nagel, J. L. Clinical outcomes of Enterobacteriaceae infections stratified by carbapenem MICs. J. Clin. Microbiol. (2015), 53:201-205.

Pemberton, O. A., et al., "Molecular basis of substrate recognition and product release by the Klebsiella pneumoniae carbapenemase (KPC-2)." J. Med. Chem. (2017), 60:3525-3530.

Penwell, W. F., et al., "Molecular mechanisms of sulbactam antibacterial activity and resistance determinants in Acinetobacter baumannii." Antimicrob. Agents Chemother. (2015), 59:1680-1689.

Pitout, J. D. D., et al., "Carbapenemase-producing Klebsiella pneumoniae, a key pathogen set for global nosocomial dominance " Antimicrob. Agents Chemother. (2015), 59:5873-5884.

Potron, A., et al., "Emerging broad-spectrum resistance in Pseudomonas aeruginosa and Acinetobacter baumannii: Mechanisms and epidemiology." Int. J Antimicrob. Agents (2015), 45:568-585.

Rastogi, N., et al., "In vitro activities of fourteen antimicrobial agents against drug susceptible and resistant clinical isolates of *Mycobacterium* tuberculosis and comparative intracellular activities against the virulent H37Rv strain in human macrophages." Curr. Microbiol. (1996), 33:167-175.

Rodrigues, F. C., et al., "Selective Killing of Dormant *Mycobacterium tuberculosis* by Marine Natural Products." Antimicrob. Agents Chemother. (2017), doi:10.1128/AAC.00743-17.

(56) References Cited

OTHER PUBLICATIONS

Rodriguez, J. G., et al., "Global adaptation to a lipid environment triggers the dormancy-related phenotype of *Mycobacterium tuberculosis.*" MBio (2014), 5:e01125-01114.
Russell, D.G., et al., "*Mycobacterium tuberculosis* wears what it eats." Cell Host Microbe (2010), 8:68-76.
Russell, D.G. "*Mycobacterium tuberculosis* and the intimate discourse of a chronic infection." Immunol. Rev. (2011), 240:252-268.
Sandhaus, S., et al., "Small Molecule Inhibitors Targeting Topoisomerase I as Novel Antituberculosis Agents." Antimicrob Agents Chemother (2016), 60(7):4028-4036.
Sauvage, E., et al., "The penicillin-binding proteins: structure and role in peptidoglycan synthesis." FEMS Microbiol. Rev. (2008), 32:234-25.
Sharma S., et al., "Simple and rapid method to determine antimycobacterial potency of compounds by using autoluminescent *Mycobacterium tuberculosis.*" Antimicrob. Agents Chemother. (2014), 58:5801-5808.
Singla, P., et al., "Extensively drug resistant tuberculosis: a mini review." Int. J. Curr. Microbiol. Appl. Sci. (2014), 3:219-234.
Tommasi, R., et al., "ESKAPEing the labyrinth of antibacterial discovery." Nat. Rev. Drug. Discov. (2015), 529-542.
Vila J, M. S., et al., "Porins, efflux pumps and multidrug resistance in Acinetobacter baumannii." J Antimicrob Chemother. (2007), 59:1210-1215.
Wolter, D. J., et al., "Mechanisms of b-lactam resistance among P. aeruginosa." Curr. Pharm. Des. (2013), 19:209-222.
Wu, P.-F., et al., "High minimum inhibitory concentration of imipenem as a predictor of fatal outcome in patients with carbapenem non-susceptible Klebsiella pneumoniae." Sci Rep. (2016), 6:32665.
Yoshimura, F., et al., "Permeability of Pseudomonas aeruginosa outer membrane to hydrophilic solutes." J. Bacteriol. (1982), 152:636-642.
Zahn, M., et al., "Structural Insights into Outer Membrane Permeability of Acinetobacter baumannii." Structure (2016), 24:221-231.
Zapun, A., et al., "Penicillin-binding proteins and β-lactam resistance." FEMS Microbiol. Rev. (2008), 32:361-385.
Zhang, J. H., et al., "A Simple Statistical Parameter for Use in Evaluation and Validation of High Throughput Screening Assays." J. Biomol. Screen (1999), 4:67-73.
Buynak, J. D. et al. Penicillin-derived inhibitors that simultaneously target both metallo- and serine-β-lactamases. Bioorg. Med. Chem. Lett. (2004), 14:1299-1304.
El Zowalaty, M. E., et al., "Pseudomonas aeruginosa: arsenal of resistance mechanisms, decades of changing resistance profiles, and future antimicrobial therapies." Future Microbiol (2015), 10:1683-1706.
Iyer, R., et al., "Whole-Cell-Based Assay to Evaluate Structure Permeation Relationships for Carbapenem Passage through the Pseudomonas aeruginosa Porin OprD." ACS Infect. Dis. (2017), 3:310-319.
King, D. T., et al., "New Delhi metallo-β-lactamase: structural insights into β-lactam recognition and inhibition." J. Am. Chem. Soc. (2012), 134:11362-11365.
Larsson, M. C., et al., "A luciferase-based assay for rapid assessment of drug activity against *Mycobacterium tuberculosis* including monitoring of macrophage viability." J. Microbiol. Methods. (2014) 106:146-150.
Nguyen, T. Q., et al., "C1β-(Aminoalkyl)carbapenem Antibiotics." ASM Microbe 2018, Atlanta, GA, USA, (2018), accepted.
Nguyen, T. Q., et al., "New Carbapenem Antibiotics with Activity against *Mycobacterium tuberculosis* and *Mycobacterium abscessus.*" ASM Microbe 2018, Atlanta, GA, (2018), USA, accepted.
Temkin, E., et al., "Carbapenem-resistant Enterobacteriaceae: biology, epidemiology, and management." Ann. N. Y. Acad. Sci. (2014), 1323:22-42.
Tommasi, R., et al., "Antibacterial Drug Discovery: Some Assembly Required." ACS Infect. Dis. (2018), https://pubs.acs.org/doi/pdf/10.1021/acsinfecdis.8b00027.
Wailan, A. M. et al., "The spread and acquisition of NDM-1: a multifactorial problem." Expert Rev. Anti Infect. Ther. (2014), 12:91-115.
Zarrilli, Raffaele., et al., "Global evolution of multidrug-resistant Acinetobacter baumannii clonal lineages." Int. J. Antimicrob. Agents (2013), 41:11-19.

\* cited by examiner $R^2 \neq H$

C5-SUBSTITUTED CARBAPENEM ANTIBIOTICS, COMPOSITIONS CONTAINING SUCH COMPOUNDS, AND METHODS OF USE IN TREATMENT OF MYCOBACTERIUM TUBERCULOSIS AND NON-TUBERCULAR MYCOBACTERIA

CROSS-REFERENCE TO RELATED APPLICATIONS

This application is a continuation of U.S. patent application Ser. No. 16/006,374, filed on Jun. 12, 2018, and claims priority to U.S. Provisional Application Ser. No. 62/518,569, filed Jun. 12, 2017, the entire contents of which are incorporated herein by reference.

STATEMENT OF FEDERALLY FUNDED RESEARCH

This invention was made with government support under AI109624 awarded by the National Institutes of Health. The government has certain rights in the invention.

TECHNICAL FIELD OF THE INVENTION

The present invention relates in general to the field of novel C5-substituted carbapenem antibiotics, compositions containing such compounds, and methods of use in the treatment of *Mycobacterium tuberculosis* and non-tubercular Mycobacteria.

BACKGROUND OF THE INVENTION

Without limiting the scope of the invention, its background is described in connection with the antibiotic resistance.

The 21$^{st}$ century is witnessing the evolution and dissemination of unprecedented levels of antimicrobial resistance and new resistance mechanisms. The evolution and dissemination of MDR, XDR, and TDR strains of *Mycobacterium tuberculosis* (Mtb) and the rise of nontuberculous Mycobacteria, make the development of new agents to treat these conditions crucial. Meropenem/clavulanate has been recently proposed as a potential treatment for Mtb, with the meropenem targeting the essential transpeptidase LdtMt2, and the clavulanic acid acting as a beta-lactamase inhibitor to protect the antibiotic from hydrolytic degradation by the beta-lactamase, BlaC. It is recognized, however, that meropenem is a broad spectrum antibiotic, with extensive antimicrobial activity against numerous strains. Long term administration of meropenem, as would be required in treatment of tuberculosis, would adversely affect the microbiome, and thus structural modifications of the carbapenem scaffold that could improve potency and selectivity for the mycobacterial l,d-transpeptidase would be extremely useful.

What is needed are novel compounds with improved activity, relative to meropenem, against both Mtb and *Mycobacterium abscessus* (Mabs).

SUMMARY OF THE INVENTION

This application concerns modified carbapenem antibiotics that exhibit enhanced activity against mycobacterial species, especially including *Mycobacterium tuberculosis* and *Mycobacterium abscessus*. These new carbapenems have a specific structural modification at the C5 position, which endows them with this improved activity. By contrast, current commercial carbapenem antibiotics all have essentially the same scaffold, with modifications occurring at the C2 position.

In one embodiment, the present invention includes a compound of formula 1, or a pharmaceutically acceptable salt thereof, comprising:

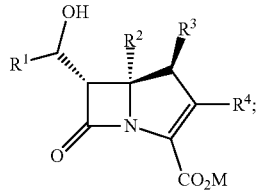

$R^1$ is H or $CH_3$ $R^2$ is not H, and is $CH_3$, or C1-C6 straight chain, or branched alkyl, or C3-C6 cycloalkyl group, or unsaturated alkenyl, including $C=CH_2$;

$R^3$ is H, $CH_3$, or a C1-C6 alkyl or cycloalkyl group, a heteroatom-substituted alkyl; and $R^4$ is a C1 to C6 alkyl, or substituted alkyl group, especially including substituents which possess positive charge, or a hydroxyl group; or $R^4$ is an $SR^a$, where $R^a$ is an unsubstituted C1 to C6 alkyl group, a substituted C1 to C6 alkyl group, or a functional group that is positively charged, or which bears a positive charge when in aqueous solution at pH 7; or $R^4$ is a $CH_2OR^b$, where $R^b$=C1 to C6 alkyl or substituted alkyl groups, substituted or unsubstituted aryl, or a heteroaryl groups.

In one aspect, $R^3$ is $(CH_2)_2NH_2$ or $(CH_2)_3NH_2$. In another aspect, $R^a$ is a substituted pyrrolidine. In another aspect, —$CO_2M$, is attached to the carbapenem nucleus at position 3, this represents a carboxylic acid group (M represents H), a carboxylate anion (M represents a negative charge), a pharmaceutically acceptable ester (M represents an ester forming group) or a carboxylic acid protected by a 30 protecting group (M represents a carboxyl protecting group). In another aspect, pharmaceutically acceptable salt is —COOM, where M is a negative charge and is balanced by a counterion. In another aspect, counterion is an alkali metal cation such as sodium, potassium, calcium, magnesium, zinc, ammonium, alkylammonium cations, tetramethylammonium, tetrabutylammonium, choline, triethylhydroammonium, or meglumine, triethanolhydroammonium. In another aspect, the —$CO_2M$ group that is attached to the carbapenem nucleus at position 3, this represents a carboxylic acid group (M represents H), a carboxylate anion (M represents a negative charge), a pharmaceutically acceptable ester (M represents an ester forming group) or a carboxylic acid protected by a 30 protecting group (M represents a carboxyl protecting group). In another aspect, the pharmaceutically acceptable salt is acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, or undecanoate. In another aspect, the molecule comprises a biolabile ester group. In another aspect, biolabile ester group is selected from at least one of pivaloyloxymethyl, acetoxymethyl, phthalidyl, indanyl, or methoxymethyl. In another aspect, M is selected from an alkoxyalkyl, alkylcarbonyloxyalkyl, alkoxycarbonyl oxyalkyl, cycloalkoxyalkyl, alkenyloxyalkyl, aryloxyalkyl, alkoxyaryl, alkylthioalkyl, cycloalkylthioalkyl, alkenylthioalkyl, arylthioalkyl or alkylthioaryl group, or the groups can be substituted in the alkyl or aryl portions thereof with acyl or halo groups, or acetoxymethyl, 1-acetoxyethyl, 1-acetoxypropyl, pivaloyloxymethyl, 1-isopropyl oxycarbonyl oxyethyl, 1-cyclohexyloxycarbonyloxyethyl, phthalidyl, or (2-oxo-5-methyl-1,3-dioxolen-4-yl)methyl. In another aspect, the compound is further combined with a beta-lactamase inhibitor, clavulanic acid or avibactam (or related DBOs), or a boronic acid based beta-lactamase inhibitor. In another aspect, the compound has the formula:

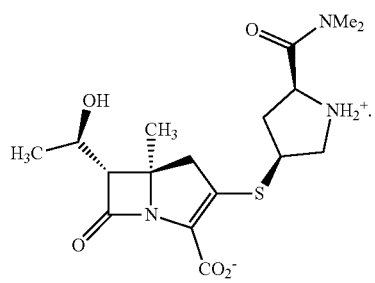

In another embodiment, the present invention includes a method of making any one of compounds 1 to 11 comprising:

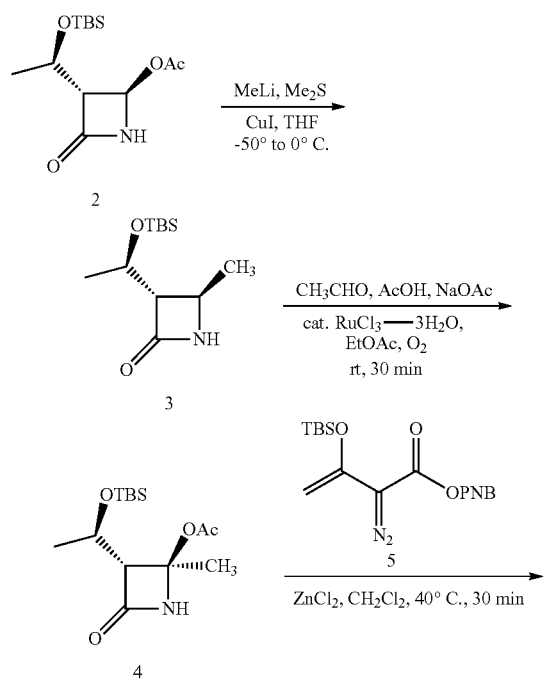

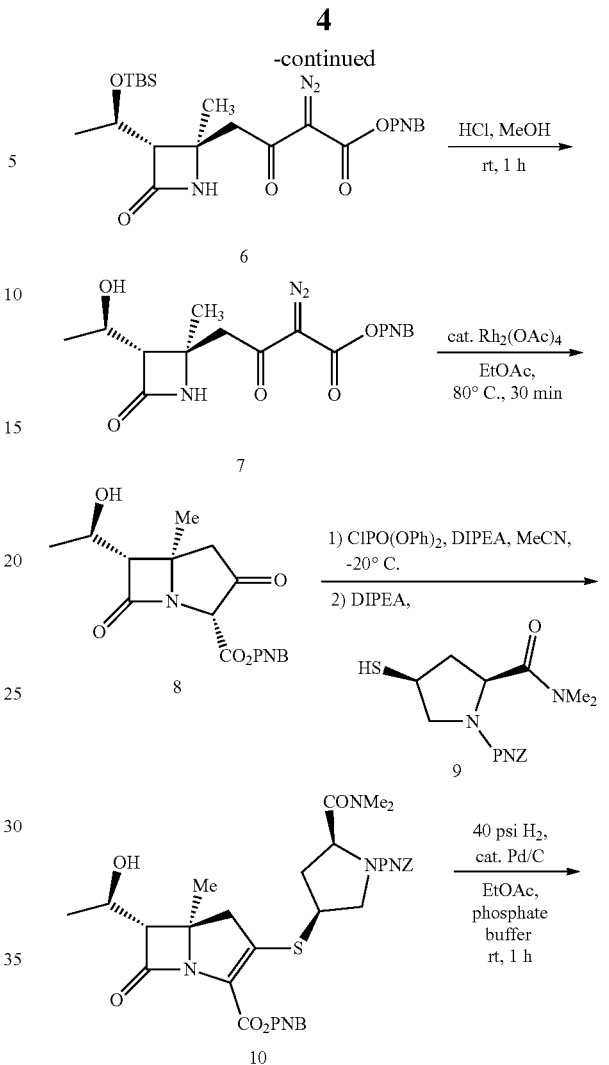

The method of claim 14, wherein the molecule has the formula:

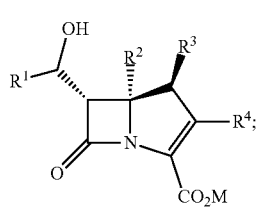

1

$R^1$ is H or $CH_3$ $R^2$ is not H, and is $CH_3$, or C1-C6 straight chain, or branched alkyl, or C3-C6 cycloalkyl group, or unsaturated alkenyl, including $C=CH_2$;

R³ is H, CH₃, or a C1-C6 alkyl or cycloalkyl group, a heteroatom-substituted alkyl; and R⁴ is a C1 to C6 alkyl, or substituted alkyl group, especially including substituents which possess positive charge, or a hydroxyl group; or R⁴ is an SR$^a$, where R$^a$ is an unsubstituted C1 to C6 alkyl group, a substituted C1 to C6 alkyl group, or a functional group that is positively charged, or which bears a positive charge when in aqueous solution at pH 7; or R⁴ is a CH₂OR$^b$, where R$^b$=C1 to C6 alkyl or substituted alkyl groups, substituted or unsubstituted aryl, or a heteroaryl groups In another embodiment, the present invention includes an antibiotic compound of formula 1, or a pharmaceutically acceptable salt thereof, comprising:

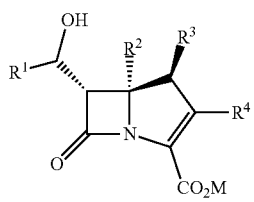

1

R¹ is H or CH₃

R² is not H, and is CH₃, or C1-C6 straight chain, or branched alkyl, or C3-C6 cycloalkyl group, or unsaturated alkenyl, including C=CH₂;

R³ is H, CH₃, or a C1-C6 alkyl or cycloalkyl group, a heteroatom-substituted alkyl; and R⁴ is a C1 to C6 alkyl, or substituted alkyl group, especially including substituents which possess positive charge, or a hydroxyl group; or R⁴ is an SR$^a$, where R$^a$ is an unsubstituted C1 to C6 alkyl group, a substituted C1 to C6 alkyl group, or a functional group that is positively charged, or which bears a positive charge when in aqueous solution at pH 7; or R⁴ is a CH₂OR$^b$, where R$^b$=C1 to C6 alkyl or substituted alkyl groups, substituted or unsubstituted aryl, or a heteroaryl groups; and one or more pharmaceutically acceptable excipients. In one aspect, R³ is (CH₂)₂NH₂ or (CH₂)₃NH₂. In another aspect, R$^a$ is a substituted pyrrolidine. In another aspect, —CO₂M, is attached to the carbapenem nucleus at position 3, this represents a carboxylic acid group (M represents H), a carboxylate anion (M represents a negative charge), a pharmaceutically acceptable ester (M represents an ester forming group) or a carboxylic acid protected by a 30 protecting group (M represents a carboxyl protecting group). In another aspect, the pharmaceutically acceptable salt is —COOM, where M is a negative charge and is balanced by a counterion. In another aspect, the counterion is an alkali metal cation such as sodium, potassium, calcium, magnesium, zinc, ammonium, alkylammonium cations, tetramethylammonium, tetrabutylammonium, choline, triethylhydroammonium, or meglumine, triethanolhydroammonium. In another aspect, the —CO₂M group that is attached to the carbapenem nucleus at position 3, this represents a carboxylic acid group (M represents H), a carboxylate anion (M represents a negative charge), a pharmaceutically acceptable ester (M represents an ester forming group) or a carboxylic acid protected by a 30 protecting group (M represents a carboxyl protecting group). In another aspect, the pharmaceutically acceptable salt is acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, or undecanoate. In another aspect, the molecule comprises a biolabile ester group. pivaloyloxymethyl, acetoxymethyl, phthalidyl, indanyl and methoxymethyl. In another aspect, the biolabile ester group is selected from at least one of pivaloyloxymethyl, acetoxymethyl, phthalidyl, indanyl, or methoxymethyl. In another aspect, M is selected from an alkoxyalkyl, alkylcarbonyloxyalkyl, alkoxycarbonyloxyalkyl, cycloalkoxyalkyl, alkenyloxyalkyl, aryloxyalkyl, alkoxyaryl, alkylthioalkyl, cycloalkylthioalkyl, alkenylthioalkyl, arylthioalkyl or alkylthioaryl group, or the groups can be substituted in the alkyl or aryl portions thereof with acyl or halo groups, or acetoxymethyl, 1-acetoxyethyl, 1-acetoxypropyl, pivaloyloxymethyl, 1-isopropyloxycarbonyloxyethyl, 1-cyclohexyloxycarbonyloxyethyl, phthalidyl, or (2-oxo-5-methyl-1,3-dioxolen-4-yl)methyl. In another aspect, the antibiotic and the one or more pharmaceutically acceptable excipients are formulated for oral, subcutaneous, topical, pulmonary, nasal, intraalveolar, parenteral, intravenous, peritoneal, or intramuscular administration. In another aspect, the antibiotic is further combined with a beta-lactamase inhibitor, clavulanic acid or avibactam (or related DBOs), or a boronic acid based beta-lactamase inhibitor. In another aspect, the compound has the formula:

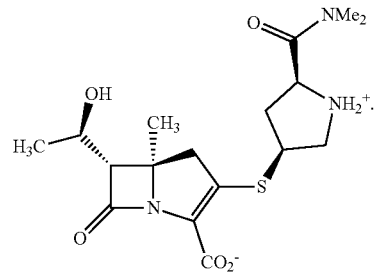

In another embodiment, the present invention includes an method of treating a bacterial infection in a subject comprising:

contacting a bacteria with an effective amount of a compound of formula I or pharmaceutically acceptable salt thereof, comprising:

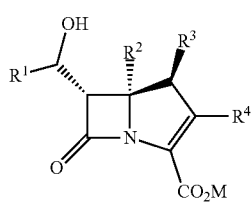

1

R¹ is H or CH₃

R² is not H, and is CH₃, or C1-C6 straight chain, or branched alkyl, or C3-C6 cycloalkyl group, or unsaturated alkenyl, including C=CH₂;

R³ is H, CH₃, or a C1-C6 alkyl or cycloalkyl group, a heteroatom-substituted alkyl; and R⁴ is a C1 to C6 alkyl, or substituted alkyl group, especially including substituents which possess positive charge, or a hydroxyl group; or R⁴ is an SR$^a$, where R$^a$ is an unsubstituted C1 to C6 alkyl group, a substituted C1 to C6 alkyl group, or a functional group that is positively charged, or which bears a positive charge when in aqueous solution at pH 7; or R⁴ is a CH₂OR$^b$, where R$^b$=C1 to C6 alkyl or substituted alkyl groups, substituted or unsubstituted aryl, or a heteroaryl groups; and wherein the compound inhibits the growth of the bacterium in the subject.

In one aspect, the method further comprises adding a beta-lactamase inhibitor, clavulanic acid or avibactam (or related DBOs), or a boronic acid based beta-lactamase inhibitor. In one aspect, R³ is (CH₂)₂NH₂ or (CH₂)₃NH₂. In another aspect, R$^a$ is a substituted pyrrolidine. In another aspect, —CO₂M, is attached to the carbapenem nucleus at position 3, this represents a carboxylic acid group (M represents H), a carboxylate anion (M represents a negative charge), a pharmaceutically acceptable ester (M represents an ester forming group) or a carboxylic acid protected by a 30 protecting group (M represents a carboxyl protecting group). In another aspect, the pharmaceutically acceptable salt is —COOM, where M is a negative charge and is balanced by a counterion. In another aspect, the counterion is an alkali metal cation such as sodium, potassium, calcium, magnesium, zinc, ammonium, alkylammonium cations, tetramethylammonium, tetrabutylammonium, choline, triethylhydroammonium, or meglumine, triethanolhydroammonium. In another aspect, the —CO₂M group that is attached to the carbapenem nucleus at position 3, this represents a carboxylic acid group (M represents H), a carboxylate anion (M represents a negative charge), a pharmaceutically acceptable ester (M represents an ester forming group) or a carboxylic acid protected by a 30 protecting group (M represents a carboxyl protecting group). In another aspect, the pharmaceutically acceptable salt is acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, or undecanoate. In another aspect, the molecule comprises a biolabile ester group. pivaloyloxymethyl, acetoxymethyl, phthalidyl, indanyl and methoxymethyl. In another aspect, the biolabile ester group is selected from at least one of pivaloyloxymethyl, acetoxymethyl, phthalidyl, indanyl, or methoxymethyl. In another aspect, M is selected from an alkoxyalkyl, alkylcarbonyloxyalkyl, alkoxycarbonyloxyalkyl, cycloalkoxyalkyl, alkenyloxyalkyl, aryloxyalkyl, alkoxyaryl, alkylthioalkyl, cycloalkylthioalkyl, alkenylthioalkyl, arylthioalkyl or alkylthioaryl group, or the groups can be substituted in the alkyl or aryl portions thereof with acyl or halo groups, or acetoxymethyl, 1-acetoxyethyl, 1-acetoxypropyl, pivaloyloxymethyl, 1-isopropyloxycarbonyloxyethyl, 1-cyclohexyloxycarbonyloxyethyl, phthalidyl, or (2-oxo-5-methyl-1,3-dioxolen-4-yl)methyl. In another aspect, the antibiotic and the one or more pharmaceutically acceptable excipients are formulated for oral, subcutaneous, topical, pulmonary, nasal, intraalveolar, parenteral, intravenous, peritoneal, or intramuscular administration. In another aspect, the antibiotic is further combined with a beta-lactamase inhibitor, clavulanic acid or avibactam (or related DBOs), or a boronic acid based beta-lactamase inhibitor. In another aspect, the compound has the formula:

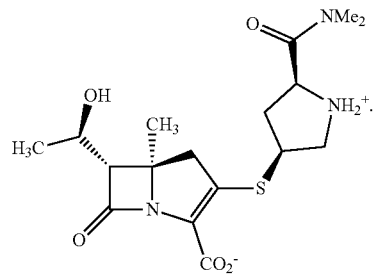

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
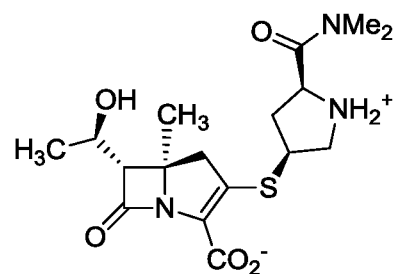
FIG. 1 is an example of C5 substituted carbapenem with enhanced anti-tubercular activity.
Figure 2:
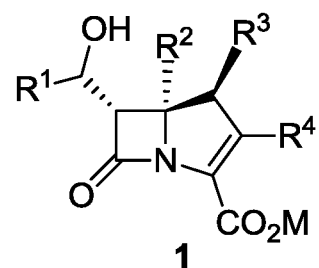
FIG. 2 shows a general structure of the new carbapenem antibiotics.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

As used herein, the terms "administration of" or "administering a" compound refers to providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like;

transdermal dosage forms, including creams, jellies, powders, or patches; buccal dosage forms; inhalation powders, sprays, suspensions, and the like; and rectal suppositories.

As used herein, the terms "effective amount" or "therapeutically effective amount" refer to an amount of compound that when provided to a the subject elicits a biological or medical response of a tissue, system, animal or human that is being sought by the researcher, veterinarian, medical doctor or other clinician. As used herein, the term "treatment" refers to the treatment of the mentioned conditions, particularly in a patient who demonstrates symptoms of the disease or disorder.

As used herein, the term "excipient" refers to one or more compatible solid or liquid filler diluents or encapsulating substances that are suitable for administration to a human subject. Some examples of substances which can serve as excipients include sugars such as lactose, glucose and sucrose; starches such as corn-starch and potato starch; cellulose and its derivatives such as sodium carboxymethylcellulose, ethylcellulose, cellulose acetate; powdered tragacanth; malt; gelatin; talc; stearic acid; magnesium stearate; calcium sulfate; vegetable oils such as peanut oil, cottonseed oil, sesame oil, olive oil, corn oil and oil of theobroma; polyols such as propylene glycol, glycerine, sorbitol, mannitol, and polyethylene glycol; agar; and alginic acid; as well as other non-toxic compatible substances used in pharmaceutical formulations. Wetting agents and lubricants such as sodium lauryl sulfate, as well as coloring agents, flavoring agents, sweetening agents (including non-nutritive sweeteners such as aspartame and saccharin), tableting agents, stabilizers, antioxidants, cooling agents, and preservatives, can also be present.

As used herein, the term "pharmaceutically acceptable" refers to a carrier, diluent, or excipient must be compatible with the other ingredients of the formulation and not be deleterious to the recipient thereof.

As used herein, the term "carrier" or "vehicle" refers to a diluent, adjuvant, excipient or vehicle with which the active compound is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents can be used. When administered to a subject, the pharmaceutically acceptable vehicles are preferably sterile. Water can be the vehicle when the active compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The present compositions, if desired, can also contain minor amounts of wetting or emulsifying agents, or pH buffering agents.

The present invention describes compounds with improved activity, relative to meropenem, against both Mtb and *Mycobacterium abscessus* (Mabs).

One molecule of the present invention has the following structure 1:

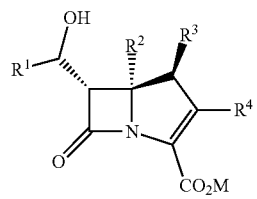

Where $R^1$=H or $CH_3$;

Where $R^2$=$CH_3$, or C1-C6 straight chain, or branched alkyl, or C3-C6 cycloalkyl group, or unsaturated alkenyl, including C=$CH_2$;

Where $R^3$ may be H, $CH_3$, or a C1-C6 alkyl or cycloalkyl group; and $R^4$ may be $SR^a$, where $R^a$=may be an unsubstituted C1 to C6 alkyl group, or substituted C1 to C6 alkyl group, especially including substituents which themselves possess a positive charge. Or alternatively $R^a$ may be a substituted or unsubstituted cyclic or heterocylic group, especially including groups which contain 1 to 3 positive charges, an aryl or heteroaryl group, or substituted aryl or heteroaryl group, particularly including a substituted pyrrolidine.

Alternatively, $R^3$ may be R3 may be heteroatom-substituted C1 to C4 alkyl, particularly including $(CH_2)_2NH_2$, or $(CH_2)_3NH_2$.

Alternatively $R^4$ may itself be $CH_2OR^b$, where $R^b$=C1 to C6 alkyl or substituted alkyl groups, substituted or unsubstituted aryl or heteroaryl groups.

With respect to —$CO_2M$, which is attached to the carbapenem nucleus at position 3, this represents a carboxylic acid group (M represents H), a carboxylate anion (M represents a negative charge), a pharmaceutically acceptable ester (M represents an ester forming group) or a carboxylic acid protected by a 30 protecting group (M represents a carboxyl protecting group).

One specific molecule is:

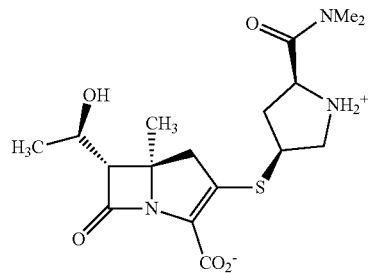

The pharmaceutically acceptable salts referred to above may take the form —COOM, where M is a negative charge, which is balanced by a counterion, e.g., an alkali metal cation such as sodium or potassium. Other pharmaceutically acceptable counterions may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable salts referred to above also include acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecyl sulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

The pharmaceutically acceptable esters are such as would be readily apparent to a medicinal chemist, and include, for example, those described in detail in U.S. Pat. No. 4,309,438. Included within such pharmaceutically acceptable esters are those that are hydrolyzed under physiological conditions, such as pivaloyloxymethyl, acetoxymethyl, phthalidyl, indanyl and methoxymethyl, and others described in detail in U.S. Pat. No. 4,479,947, relevant portions incorporated herein by reference. These are also referred to as "biolabile esters".

Biolabile esters are biologically hydrolizable, and may be suitable for oral administration, due to good absorption through the stomach or intestinal mucosa, resistance to gastric acid degradation and other factors. Examples of biolabile esters include compounds in which M represents an alkoxyalkyl, alkylcarbonyloxyalkyl, alkoxycarbonyloxyalkyl, cycloalkoxyalkyl, alkenyloxyalkyl, aryloxyalkyl, alkoxyaryl, alkylthioalkyl, cycloalkylthioalkyl, alkenylthioalkyl, arylthioalkyl or alkylthioaryl group. These groups can be substituted in the alkyl or aryl portions thereof with acyl or halo groups. The following M species are examples of biolabile ester forming moieties: acetoxymethyl, 1-acetoxyethyl, 1-acetoxypropyl, pivaloyloxymethyl, 1-isopropyloxycarbonyloxyethyl, 1-cyclohexyloxycarbonyloxyethyl, phthalidyl and (2-oxo-5-methyl-1,3-dioxolen-4-yl)methyl.

The synthetic methodology that was employed to make these new carbapenems is shown in Scheme 1.

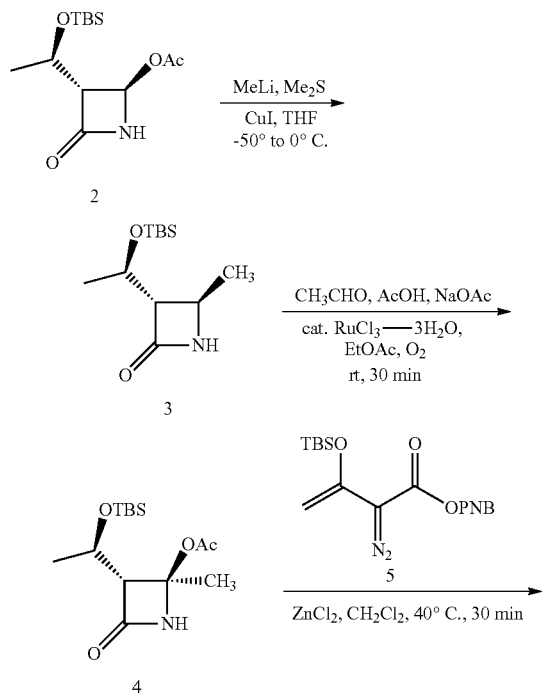

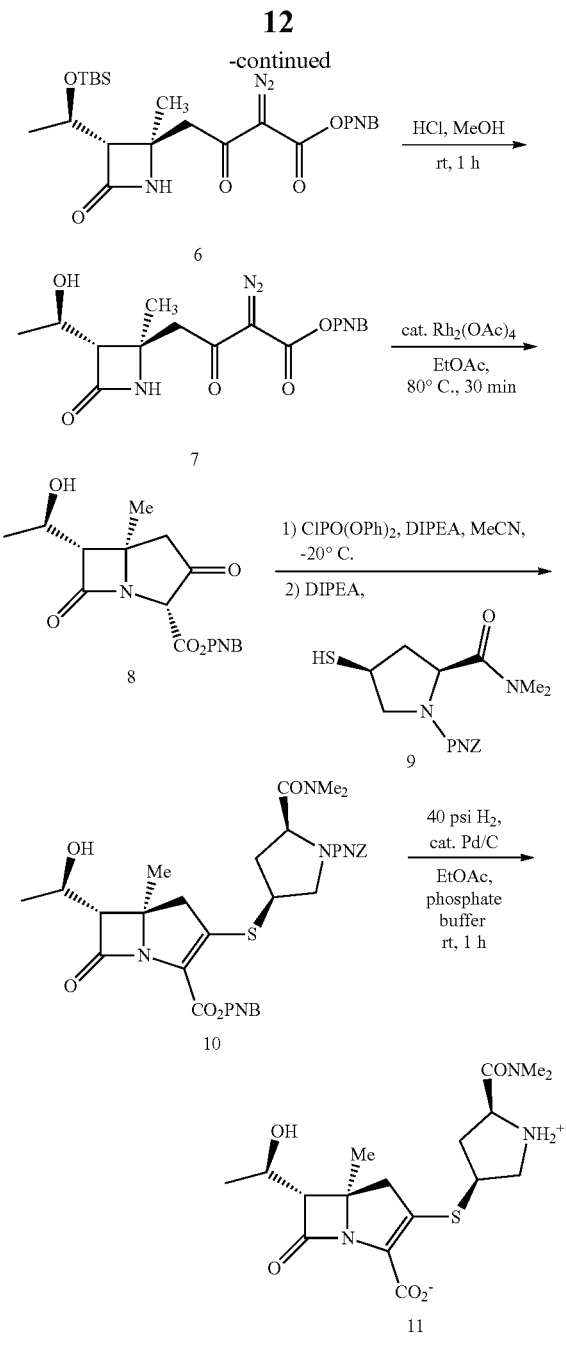

Scheme 1 involves the preparation of carbapenems of general structure 2. The detailed synthetic methodology utilized to prepare these novel carbapenems is provided below.

(3S,4R)-4-methyl-3-[1(R)-(t-butyldimethylsilyloxy)ethyl]azetidin-2-one (3)

Dimethyl sulfide (0.2 mol) was added to a slurry of copper (I) iodide (0.2 mol) in THF at room temperature and stirred for 10 min. The resultant solution was cooled to −50° C. and treated with methyllithium (0.4 mol, 1.6 M solution in Et$_2$O). The reaction was then allowed to warm to −10° C. for 20 min, and cooled back to −50° C. Then compound 2 was added (as a solid), and the reaction was warmed to rt over the course of 1 h. After completion, the resulting mixture was treated with aq NH$_4$Cl and the THF evaporated in vacuo. The resultant material was diluted with $CH_2Cl_2$ and washed with $NH_4Cl$, water and brine, dried over sodium sulfate and concentrated.

Yield 87%, $^1$H NMR (400 MHz, $CDCl_3$): δ 0.09 (s, 6H), 0.90 (s, 9H), 1.23 (d, J=6.24, 2H), 1.35 (d, J=6.07, 2H), 2.83 (m, 1H), 3.85 (m, 1H), 4.21 (m, 1H), 5.78 (s, 1H).

(3S,4R)-4-acetoxy-4-methyl-3-[1(R)-(t-butyldimethylsilyloxy)ethyl]azetidin-2-one (4)

To a solution of compound 3 (12.0 mmol) in EtOAc (80 mL), acetic acid (6 mL) was added followed by $RuCl_3·3H_2O$ (0.62 mmol) and NaOAc (3 mmol) at rt. Then freshly distilled $CH_3CHO$ (1.5 mL) was added quickly and the atmosphere was replaced with an oxygen balloon.

The reaction mixture was stirred for 15 min and $CH_3CHO$ (1.5 mL) was added again. The reaction was allowed to stir for another 15 min. After the reaction was completed, diluted with EtOAc (100 mL) and the organic layer was washed by $NaHCO_3$, water and dried over sodium sulfate then purified through column.

Yield 75%, $^1$H NMR (400 MHz, $CDCl_3$): δ 0.15 (m, 6H), 0.95 (s, 9H), 1.45 (d, J=6.13, 3H), 1.98 (s, 3H), 2.12 (s, 3H), 3.18 (d, J=7.12, 1H), 4.33 (m, 1H), 6.95 (s, 1H).

(3R,4S)-4-(p-Nitrobenzyl-2-diazoacetoacetate)-4-methyl-3-[1(R)-(t-butyldimethylsilyloxy)ethyl]azetidin-2-one (6)

To a solution of compound 4 (9.3 mol) in anhydrous $CH_2Cl_2$ (100 mL), compound 5 (18.6 mol) and $ZnCl_2$ (4.7 mL, 1 M solution in $Et_2O$) was added. The resulting mixture was stirred for 30 min at 40° C. After the reaction was completed, diluted with $CH_2Cl_2$ (100 mL), washed with $NaHCO_3$, water and brine, dried over sodium sulfate, evaporated the solvent in vacuo and purified through column.

Yield 51%, $^1$H NMR (400 MHz, $CDCl_3$): δ 0.18 (s, 6H), 0.98 (s, 9H), 2.23 (d, J=6.07, 3H), 2.56 (s, 3H), 3.55 (m, 1H), 4.31 (m, 1H), 5.44 (s, 2H), 7.61 (d, J=7.95, 2H), 8.35 (d, J=8.05, 2H).

(3R,4S)-4-(p-Nitrobenzyl-2-diazoacetoacetate)-4-methyl-3-(1-hydroxyethyl)azetidin-2-one (7)

To a solution of compound 6 (1.8 g) in MeOH (8 mL), HCl (8 mL, solution in water 5 M) was added and the reaction at rt and stirred for 1 h. After the reaction was completed, the solvent was evaporated in vacuo and the product was used for the next step.

Yield 95%, $^1$H NMR (400 MHz, $CDCl_3$): δ 1.39 (d, J=6.12, 3H), 1.56 (s, 3H), 2.91 (d, J=10.32, 1H), 3.32 (d, J=2.56, 2H), 4.16 (s, J=5.72, 1H), 5.33 (s, 2H), 7.56 (d, J=7.96, 2H), 8.24 (d, J=8.04, 2H).

(2R,5R,6S)-5-methyl-4-Nitrobenzyl ester-6-((R)-1-hydroxyethyl)-3,7-dioxo-1-azabicyclo[3.2.0]heptane-2-carboxylic acid (8)

To a solution of compound 7 (3.8 mmol) in EtOAc 15 mL, $Rh_2(OAc)_4$ (0.19 mmol) was added. The reaction mixture was heated to reflux for 30 min. After the reaction was completed, the solvent was evaporated in vacuo the product was used directly for the next step.

Yield 99%, $^1$H NMR (400 MHz, $CDCl_3$): δ 1.48 (q, J=6.20, 2H), 1.60 (d, J=6.04, 2H), 2.59 (q, J=16.2, 2H), 3.22 (d, J=9.88, 1H), 4.39 (m, 1H), 5.27 (m, 2.02), 7.56 (d, J=8.76, 2H), 8.25 (d, J=8.12, 2H).

(5R,6S)-5-methyl-3-[[(3S,5S)$_5$-[(dimethylamino)carbonyl]-1-[[(4-nitrophenyl)methoxy]carbonyl]-3-pyrrolidinyl]thio]-4-Nitrobenzyl-6-((R)-1-hydroxyethyl)-7-oxo-1-azabicyclo[3.2.0]hept-2-ene-2-carboxylate (10)

To a solution of compound 8 (2 mmol) in dry acetonitrile (8 mL), diphenylphosphoryl chloride (2 mmol) and (iPr)$_2$NEt (2 mmol) was added −40° C. The reaction mixture was stirred for 20 min and allowed to warm to −10° C. Then compound 9 (2 mmol) was added to the previous mixture followed by diisopropylethylamine (2 mmol) at −40° C. The reaction was stirred for 30 min at −40° C. Then the resulting mixture was diluted with EtOAc (30 mL), and the organic layer was washed with $NaHCO_3$, $NH_4Cl$ and brine, concentrated in vacuo and purified by column.

Yield 35%, $^1$H NMR (400 MHz, $CDCl_3$): δ 1.44 (d, J=5.72, 2H), 1.61 (d, J=3.96, 2H), 3.00 (2d, 6H), 3.15 (d, J=3.84, 1H), 3.56 (m, 2H), 4.28 (m, 1H), 5.12 (d, J=8.68, 1H), 5.22 (m, 4H), 5.30 (d, J=8.34, 1H), 5.52 (d, J=13.8, 1H), 7.45 (m, 4H), 8.23 (m, 4H).

(5R,6S)-5-methyl-3-[[(3S,5S)5-[(dimethylamino)carbonyl-3-pyrrolidinyl]thio]-6-((R)-1-hydroxyethyl)-7-oxo-1-azabicyclo[3.2.0]hept-2-ene)-2-carboxylate Acid 11

A slurry of compound 10 (300 mg, 0.422 mmol) with Pd/C (300 mg) in EtOAc (20 mL) and buffer (pH=6, 20 mL) was shaken on a Parr hydrogenator at 50 psi $H_2$ pressure for 90 min. The solution was then filtered through celite to remove the catalyst. The aqueous layer was separated and washed with ether, then concentrated and purified through column.

Yield 19%, $^1$H NMR (400 MHz, $D_2O$): δ 1.17 (d, J=5.43, 3H), 1.83 (m, 1H), 1.92 (m, 1H), 2.75 (m, 2H), 2.93 (m, 6H), 3.28 (m, 2H), 3.65 (m, 2H), 3.85 (m, 1H), 4.12 (m, 1H).

Data on Compound 11

TABLE 1

| MIC values (M) of selected carbapenems against Mtb and Mab | | |
|---|---|---|
| Compound | Mtb | Mabs |
| Meropenem | 0.83 | 3.25 |
| 11 | 0.47 | 0.73 |

The following additional terms are as defined herein. The term "alkyl", "alkenyl", "alkynyl" and "alkylene" denotes hydrocarbon chains typically ranging from about 1 to about 12 carbon atoms in length, preferably 1 to about 6 atoms, and includes straight and branched chains. Unless otherwise noted, in one embodiment of any alkyl or alkylene referred to herein is C1-C6 alkyl (e.g., methyl or ethyl).

The term "cycloalkyl" denotes a saturated or unsaturated cyclic hydrocarbon chain, including bridged, fused, or spiro cyclic compounds, preferably comprising 3 to about 12 carbon atoms, more preferably 3 to about 8.

The term "aryl" denotes one or more aromatic rings, each of 5 or 6 core carbon atoms. Multiple aryl rings may be fused, as in naphthyl or unfused, as in biphenyl. Aryl rings may also be fused or unfused with one or more cyclic hydrocarbon, heteroaryl, or heterocyclic rings.

The term "heteroaryl" denotes an aryl group containing from one to four heteroatoms, preferably N, O, or S, or a combination thereof, which heteroaryl group is optionally substituted at carbon or nitrogen atom(s) with C1-C6 alkyl, —$CF_3$, phenyl, benzyl, or thienyl, or a carbon atom in the heteroaryl group together with an oxygen atom form a carbonyl group, or which heteroaryl group is optionally fused with a phenyl ring. Heteroaryl rings may also be fused with one or more cyclic hydrocarbon, heterocyclic, aryl, or heteroaryl rings. Heteroaryl includes, but is not limited to, 5-membered heteroaryls having one hetero atom (e.g., thiophenes, pyrroles, furans); 5-membered heteroaryls having two heteroatoms in 1,2 or 1,3 positions (e.g., oxazoles, pyrazoles, imidazoles, thiazoles, purines); 5-membered heteroaryls having three heteroatoms (e.g., triazoles, thiadiazoles); 5-membered heteroaryls having 3 heteroatoms; 6-membered heteroaryls with one heteroatom (e.g., pyridine, quinoline, isoquinoline, phenanthrine, 5,6-cycloheptenopyridine); 6-membered heteroaryls with two heteroatoms (e.g., pyridazines, cinnolines, phthalazines, pyrazines, pyrimidines, quinazolines); 6-membered heteroaryls with three heteroatoms (e.g., 1,3,5-triazine); and 6-membered heteroaryls with four heteroatoms.

The term "heterocycle" or "heterocyclic" denotes one or more rings of 5-12 atoms, preferably 5-7 atoms, with or without unsaturation or aromatic character and at least one ring atom which is not carbon. Preferred heteroatoms include sulfur, oxygen, and nitrogen. Multiple rings may be fused.

The term "heteroatom" denotes any non-carbon atom in a hydrocarbon analog compound. Examples include oxygen, sulfur, nitrogen, phosphorus, arsenic, silicon, selenium, tellurium, tin, and boron.

The term "alkylene" denotes a divalent alkyl group as defined above, such as methylene (—CH2-), propylene (—CH2 CH2 CH2-), chloroethylene (—CHClCH2-), 2-thiobutene —CH2 CH(SH)CH2 CH2, 1-bromo-3-hydroxyl-4-methylpentene (—CHBrCH2 CH(OH)CH(CH3) CH2-), and the like.

The term "alkenyl" denotes branched or unbranched hydrocarbon chains containing one or more carbon-carbon double bonds.

The term "alkynyl" denotes branched or unbranched hydrocarbon chains containing one or more carbon-carbon triple bonds.

The term "aryl" denotes a chain of carbon atoms which form at least one aromatic ring having preferably between about 6-14 carbon atoms, such as phenyl, naphthyl, and the like, and which may be substituted with one or more functional groups which are attached commonly to such chains, such as hydroxyl, bromo, fluoro, chloro, iodo, mercapto or thio, cyano, cyanoamido, alkylthio, heterocycle, aryl, heteroaryl, carboxyl, carbalkoyl, alkyl, alkenyl, nitro, amino, alkoxyl, amido, and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, amidophenyl, thiazolylphenyl, oxazolylphenyl, imidazolylphenyl, imidazolylmethylphenyl, and the like.

The term "alkoxy" denotes —OR—, wherein R is alkyl.

The term "amido" denotes an amide linkage: —C(O)NHR (wherein R is hydrogen or alkyl).

The term "amino" denotes an amine linkage: —NR—, wherein R is hydrogen or alkyl. The term "carboxyl" denotes —C(O)O—, and the term "carbonyl" denotes —C(O)—.

The term "alkylcarboxyl" denote an alkyl group as defined above substituted with a C(O)O group, for example, CH3 C(O)O—, CH3 CH2 C(O)O—, etc.

The term "carbocycle" denotes cyclic hydrocarbon chain having about 5 to about 8 ring carbons such as cyclopentyl, cylcohexyl, etc. These groups can be optionally substituted with one or more functional groups as defined under "alkyl" above.

The term "halogen" includes chlorine, fluorine, bromine, iodine and mixtures thereof The term "heterocycle" denotes straight chain or ring system that may contain from zero to four heteroatoms selected from N, O, and S, wherein the nitrogen and sulfur atoms are optionally oxidized, and the nitrogen atom(s) are optionally quaternized.

The term "carbamoyl" denotes the group —C(O)NH2.

The term "hydroxyalkyl" denotes an alkyl group as defined above which is substituted by a hydroxy group.

The term "alkylcarbonyl", alone or in combination, means an acyl group derived from an alkanecarboxylic acid, i.e. alkyl-C(O)—, such as acetyl, propionyl, butyryl, valeryl, 4-methylvaleryl etc.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "con-

What is claimed is:

1. A compound of formula 1, or a pharmaceutically acceptable salt thereof, comprising:

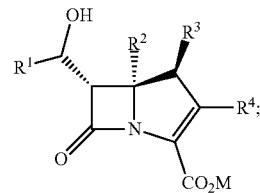

$R^1$ is H or $CH_3$ $R^2$ is not H, and is $CH_3$, or C1-C6 straight chain, or branched alkyl, or C3-C6 cycloalkyl group, or unsaturated alkenyl, including $C=CH_2$;

$R^3$ is H, $CH_3$, or a C1-C6 alkyl or cycloalkyl group, a heteroatom-substituted alkyl; and $R^4$ is a C1 to C6 alkyl, substituted alkyl group, or a substituent with a positive charge, or a hydroxyl group; or $R^4$ is an $SR^a$, where $R^a$ is an unsubstituted C1 to C6 alkyl group, a substituted C1 to C6 alkyl group; or $R^4$ is a $CH_2OR^b$, where $R^b$=C1 to C6 alkyl or substituted alkyl groups, substituted or unsubstituted aryl, or a heteroaryl groups; and wherein M is a carboxylic acid group, M is a negative charge in a carboxylate anion, M is an ester-forming group of a pharmaceutically acceptable ester, or M is a carboxyl protecting group of a carboxylic acid.

2. The compound of claim 1, wherein $R^3$ is $(CH_2)_2NH_2$ or $(CH_2)_3NH_2$.

3. The compound of claim 1, wherein —$CO_2M$ is attached to the carbapenem nucleus at position 3 or a carboxylic acid group.

4. The compound of claim 1, wherein M has a negative charge and is balanced by a counterion, wherein the counterion is an alkali metal cation selected from sodium, potassium, calcium, magnesium, zinc, ammonium, alkylammonium cations, tetramethylammonium, tetrabutylammonium, choline, triethylhydroammonium, or meglumine, triethanolhydroammonium.

5. The compound of claim 1, wherein the pharmaceutically acceptable salt is acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, or undecanoate.

6. The compound of claim 1, wherein the molecule comprises a biolabile ester group.

7. The compound of claim 6, wherein the biolabile ester group is selected from at least one of pivaloyloxymethyl, acetoxymethyl, phthalidyl, indanyl, or methoxymethyl.

8. The compound of claim 1, wherein M is selected from an alkoxyalkyl, alkylcarbonyloxyalkyl, alkoxycarbonyloxyalkyl, cycloalkoxyalkyl, alkenyloxyalkyl, aryloxyalkyl, alkoxyaryl, alkylthioalkyl, cycloalkylthioalkyl, alkenylthioalkyl, arylthioalkyl or alkylthioaryl group, or the groups can be substituted in the alkyl or aryl portions thereof with acyl or halo groups, or acetoxymethyl, 1-acetoxyethyl, 1-acetoxypropyl, pivaloyloxymethyl, 1-isopropyloxycarbonyloxyethyl, 1-cyclohexyloxycarbonyloxyethyl, phthalidyl, or (2-oxo-5-methyl-1,3-dioxolen-4-yl)methyl.

9. The compound of claim 1, wherein the compound is further combined with a beta-lactamase inhibitor, clavulanic acid or avibactam, or a boronic acid based beta-lactamase inhibitor.

10. A method of making any one of compounds 1 to 11 comprising:

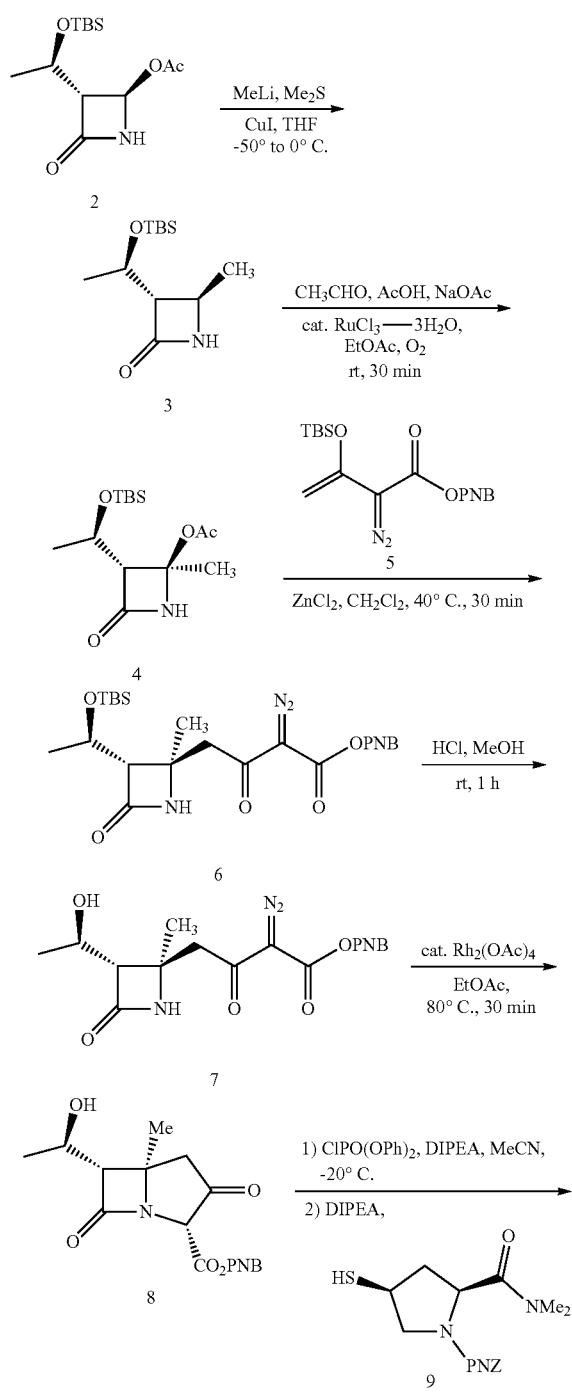

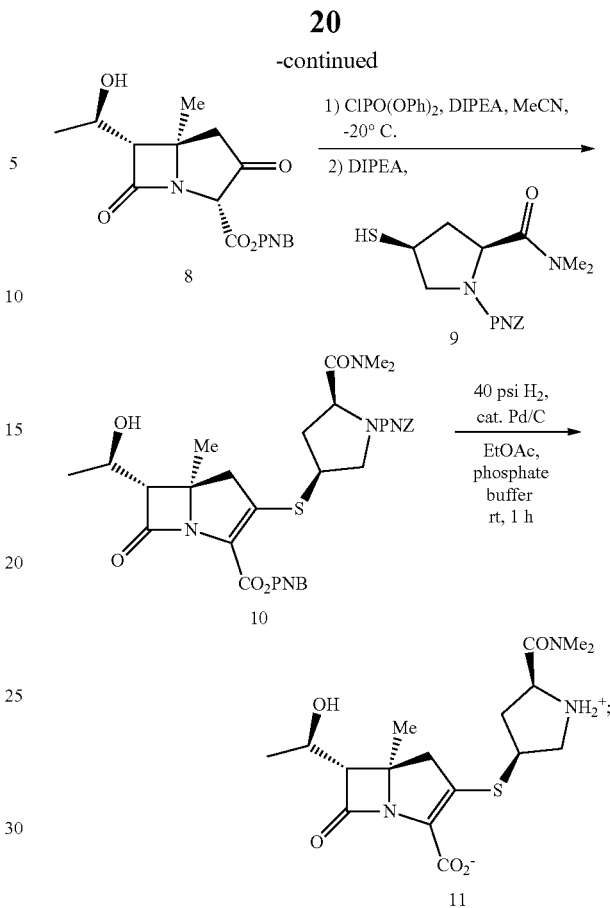

and wherein the molecule has the formula 1

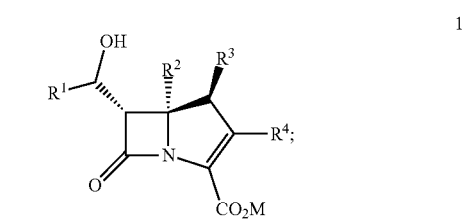

$R^1$ is H or $CH_3$ $R^2$ is not H, and is $CH_3$, or C1-C6 straight chain, or branched alkyl, or C3-C6 cycloalkyl group, or unsaturated alkenyl, including $C=CH_2$;

$R^3$ is H, $CH_3$, or a C1-C6 alkyl or cycloalkyl group, a heteroatom-substituted alkyl; and $R^4$ is a C1 to C6 alkyl, or substituted alkyl group, especially including substituents which possess positive charge, or a hydroxyl group; or $R^4$ is an $SR^a$, where $R^a$ is an unsubstituted C1 to C6 alkyl group, a substituted C1 to C6 alkyl group; or $R^4$ is a $CH_2OR^b$, where $R^b$=C1 to C6 alkyl or substituted alkyl groups, substituted or unsubstituted aryl, or a heteroaryl groups; and wherein M is a carboxylic acid group, M is a negative charge in a carboxylate anion, M is an ester-forming group of a pharmaceutically acceptable ester, or M is a carboxyl protecting group of a carboxylic acid.

11. An antibiotic compound of formula 1, or a pharmaceutically acceptable salt thereof, comprising:

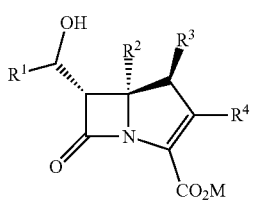

R¹ is H or CH₃

R² is not H, and is CH₃, or C1-C6 straight chain, or branched alkyl, or C3-C6 cycloalkyl group, or unsaturated alkenyl, including C=CH₂;

R³ is H, CH₃, or a C1-C6 alkyl or cycloalkyl group, a heteroatom-substituted alkyl; and R⁴ is a C1 to C6 alkyl, or substituted alkyl group, especially including substituents which possess positive charge, or a hydroxyl group; or R⁴ is an SR$^a$, where R$^a$ is an unsubstituted C1 to C6 alkyl group, a substituted C1 to C6 alkyl group, or a functional group that is positively charged, or has a positive charge in aqueous solution at pH 7; or R⁴ is a CH₂OR$^b$, where R$^b$=C1 to C6 alkyl or substituted alkyl groups, substituted or unsubstituted aryl, or a heteroaryl groups, wherein M is a carboxylic acid group, M is a negative charge of a carboxylate anion, M is an ester forming group of a pharmaceutically acceptable ester, or M is a carboxyl protecting group of a carboxylic acid; and one or more pharmaceutically acceptable excipients.

12. The antibiotic of claim 11, wherein R³ is (CH₂)₂NH₂ or (CH₂)₃NH₂.

13. The antibiotic of claim 11, wherein a —CO₂M is attached to the carbapenem nucleus at position 3.

14. The antibiotic of claim 11, wherein the pharmaceutically acceptable salt is —COOM, where M is a negative charge and is balanced by a counterion.

15. The antibiotic of claim 14, wherein the counterion is an alkali metal cation selected from sodium, potassium, calcium, magnesium, zinc, ammonium, alkylammonium cations, tetramethylammonium, tetrabutylammonium, choline, triethylhydroammonium, or meglumine, triethanolhydroammonium.

16. The antibiotic of claim 11, wherein the pharmaceutically acceptable salt is acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, or undecanoate.

17. The antibiotic of claim 11, wherein the compound comprises a biolabile ester group, pivaloyloxymethyl, acetoxymethyl, phthalidyl, indanyl or methoxymethyl.

18. The antibiotic of claim 11, wherein M is selected from an alkoxyalkyl, alkylcarbonyloxyalkyl, alkoxycarbonyloxyalkyl, cycloalkoxyalkyl, alkenyloxyalkyl, aryloxyalkyl, alkoxyaryl, alkylthioalkyl, cycloalkylthioalkyl, alkenylthioalkyl, arylthioalkyl or alkylthioaryl group, or the groups can be substituted in the alkyl or aryl portions thereof with acyl or halo groups, or acetoxymethyl, 1-acetoxyethyl, 1-acetoxypropyl, pivaloyloxymethyl, 1-isopropyloxycarbonyloxyethyl, 1-cyclohexyloxycarbonyloxyethyl, phthalidyl, or (2-oxo-5-methyl-1,3-dioxolen-4-yl)methyl.

19. The antibiotic of claim 11, wherein the antibiotic and the one or more pharmaceutically acceptable excipients are formulated for oral, subcutaneous, topical, pulmonary, nasal, intraalveolar, parenteral, intravenous, peritoneal, or intramuscular administration.

20. The antibiotic of claim 11, is further combined with a beta-lactamase inhibitor, clavulanic acid or avibactam, or a boronic acid based beta-lactamase inhibitor.

21. The antibiotic of claim 11, wherein the compound has the formula:

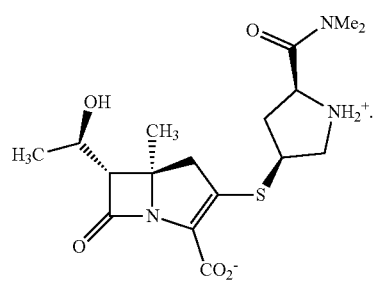

22. A method of treating a *Mycobacterium* sp. infection in a subject comprising:

contacting the *Mycobacterium* sp. with an effective amount of a compound of formula I or pharmaceutically acceptable salt thereof, comprising:

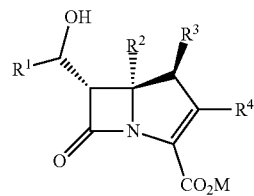

R¹ is H or CH₃

R² is not H, and is CH₃, or C1-C6 straight chain, or branched alkyl, or C3-C6 cycloalkyl group, or unsaturated alkenyl, including C=CH₂;

R³ is H, CH₃, or a C1-C6 alkyl or cycloalkyl group, a heteroatom-substituted alkyl; and R⁴ is a C1 to C6 alkyl, or substituted alkyl group, especially including substituents which possess positive charge, or a hydroxyl group; or R⁴ is an SR$^a$, where R$^a$ is an unsubstituted C1 to C6 alkyl group, a substituted C1 to C6 alkyl group, or a functional group that is positively charged, or which bears a positive charge when in aqueous solution at pH 7; or R⁴ is a CH₂OR$^b$, where R$^b$=C1 to C6 alkyl or substituted alkyl groups, substituted or unsubstituted aryl, or a heteroaryl groups, wherein M is a carboxylic acid group, M is a negative charge of a carboxylate anion, M is an ester forming group of a pharmaceutically acceptable ester, or M is a carboxyl protecting group of a carboxylic acid; and wherein the compound inhibits the growth of the bacterium in the subject.

* * * * *